(12) United States Patent
Bissery

(10) Patent No.: US 6,933,320 B2
(45) Date of Patent: Aug. 23, 2005

(54) COMBINATION COMPRISING COMBRETASTATIN AND ANTICANCER AGENTS

(75) Inventor: Marie-Christine Bissery, Vitry sur Seine (FR)

(73) Assignee: Aventis Pharma S. A., Antony Cedex (FR)

( * ) Notice: Subject to any disclaimer, the term of this patent is extended or adjusted under 35 U.S.C. 154(b) by 243 days.

(21) Appl. No.: 10/097,926

(22) Filed: Mar. 15, 2002

(65) Prior Publication Data

US 2003/0060429 A1 Mar. 27, 2003

Related U.S. Application Data

(60) Provisional application No. 60/275,627, filed on Mar. 15, 2001.

(51) Int. Cl.⁷ .............................................. A61K 31/135
(52) U.S. Cl. ........................... 514/646; 514/23; 514/34; 514/283; 514/449; 514/598; 514/617; 514/619; 514/620; 514/626; 514/630; 514/716; 514/718; 514/720; 514/922; 424/649
(58) Field of Search ................................ 514/617, 619, 514/620, 626, 630, 646, 716, 718, 720, 922, 449, 23, 34, 598, 283; 424/649

(56) References Cited

U.S. PATENT DOCUMENTS

| | | | |
|---|---|---|---|
| 4,857,653 A | | 8/1989 | Colin et al. |
| 4,996,237 A | | 2/1991 | Pettit et al. |
| 5,430,062 A | | 7/1995 | Cushman et al. |
| 5,525,632 A | | 6/1996 | Obsumi et al. |
| 5,561,122 A | | 10/1996 | Pettit |
| 5,674,906 A | * | 10/1997 | Hatanaka et al. ........... 514/626 |
| 5,731,353 A | | 3/1998 | Ohsumi et al. |
| 6,462,087 B1 | * | 10/2002 | Morinaga et al. ........... 514/598 |
| 6,562,834 B2 | * | 5/2003 | Bissery |

FOREIGN PATENT DOCUMENTS

| | | |
|---|---|---|
| EP | 0 253 738 | 1/1988 |
| EP | 0 253 739 | 1/1988 |
| WO | WO 92/09589 | 6/1992 |
| WO | WO 02/056692 A1 * | 7/2002 |

OTHER PUBLICATIONS

Corbett, T.H., et al., "Evaluation of Single Agents and Combinations of Chemotherapeutic Agents in Mouse Colon Carcinomas," *Cancer*, 40(5), 1977, pp. 2660–2680.

Corbett, T.H., et al., "Response of Transplantable Tumors of Mice to Anthracenedione Derivatives Alone and in Combination With Clinically Useful Agents," *Cancer Treatment Reports*, 66(5), 1982, pp. 1187–1200.

Schabel, Jr., F.M., et al., "Testing Therapeutic Hypotheses in Mice and Man: Observations on the Therapeutic Acitvity Against Advanced Solid Tumors of Mice Treated with Anticancer Drugs that have Demonstrated or Potential Clinical Utility for Treatment of Advanced Solid Tumors of Man," *Cancer Drug Development, Part B, Methods in Cancer Research*, 17, 1979, pp. 3–51.

William J. Slichenmyer et al., The Current Status of Camptothecin Analogues as Antitumor Agents, *J. Nat. Cancer Inst.*, 85:271–285 (1993).

* cited by examiner

*Primary Examiner*—Frederick Krass
(74) *Attorney, Agent, or Firm*—Balaram Gupta

(57) ABSTRACT

An antitumor combination comprising a stilbene derivative and an anticancer compound selected from the group consisting of taxanes, alkylating agents, antimetabolites, vinca alkaloids, platinum compounds, epidophylloptoxins, and antibiotics as the active ingredients is provided. Methods of using these pharmaceutical preparations for the treatment of solid carcinomas and the like are also provided.

8 Claims, No Drawings

COMBINATION COMPRISING COMBRETASTATIN AND ANTICANCER AGENTS

This application relies on the benefit of priority of U.S. provisional application No. 60/275,627, filed Mar. 15, 2001.

FIELD OF INVENTION

The present invention relates to therapeutic combinations comprising a stilbene derivative and anticancer agents such as taxanes, alkylating agents, antimetabolites, vinca alkaloids, epidophylloptoxins, and antibiotics for the treatment for cancer.

The invention relates to the treatment of cancers, more especially solid tumors, with associations of stilbene derivatives and other anticancer drugs and the use of such associations for an improved treatment against cancers, and to uses of these effective ingredients for the treatment (therapy), suppression, and amelioration of tumors, and the like.

BACKGROUND OF THE INVENTION

Today, a wide variety of chemotherapeutic agents are used for treatment, and suppression of tumors, especially malignant solid tumors. Although these agents may have a tumor reducing effect, it is often not possible for these known agents to effect a cure due to acquisition of resistance against the agent by the cancer, relapse of the tumors, and so on. Therefore, further superior antitumor agents are needed.

While stilbene derivatives, having cis-stilbene as a fundamental skeleton, are known to exhibit strong mitosis inhibitory activities and cytotoxicity, most stilbene derivatives are not yet available as pharmaceutical agents because of their low solubility in water.

Recently, it has been discovered that certain stilbene derivatives having activity for inhibiting tubulin polymerization also have improved water solubility. These include the phosphorylated pro-drug of combretastatin-A4 (See U.S. Pat. No. 5,561,122), and the stilbene derivatives disclosed in U.S. Pat. No. 5,674,906. The clinical use of these stilbene derivatives is felt to be promising. However, more work is needed to improve the efficacy of these and other stilbene derivatives.

It is an object of the present invention to develop a superior antitumor agent, specifically, to develop a pharmaceutical preparation capable of improving the efficacy of a stilbene derivative and, in particular, to develop and provide antitumor agents exhibiting superior safety and efficacy in treating malignant tumors.

SUMMARY OF THE INVENTION

It has been found that a stilbene derivative, administered together with another anticancer agent such as a taxane, an alkylating agent, an antimetabolite, an epidophylloptoxin, an antibiotic, a platinum compound, and a vinca alkaloid, exhibit improved therapeutic effects to inhibit tumor growth.

Among substances which may be used in association or in combination with the stilbene derivative are taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins.

Taxanes such as taxol and taxotere and vinca alkaloids such as vincristine and vinblastine are considered antimicrotubule agents which interfere with cell division by disrupting the normal functionality of the cellular microtubules. Alkylating agents such as cyclophosphamide, isosfamide, melphalan, hexamethylmelamine, thiotepa or dacarbazine generally exert cytotoxic activity by alkylating DNA, thus directly interfering with the reproductive cycle of the cell. Antimetabolites exert cytotoxic activity by substituting fraudulent nucleotides into cellular DNA, thereby interrupting cell division or inhibiting enzymes which are necessary for DNA replication. Epidophylloptoxins such as etoposide and teniposide are topoisomerase inhibitors. Antibiotics, such as doxorubicin and daunorubicin, are also thought to work by inhibiting topoisomerase II.

It has now been found that these various anticancer agents in combination with a stilbene derivative are especially effective in the treatment of many solid tumors. Among the effective stilbene derivatives is combretastatin A-4, and a derivative of the compound (Z)-1-(3-amino-4-methoxyphenyl)-2-(3,4,5-trimethoxyphenyl)ethene. Both of these compounds exhibit strong mitosis inhibitory activities, cytotoxicity, and inhibit tubulin polymerization.

Combretastatin A-4 has the following formula:

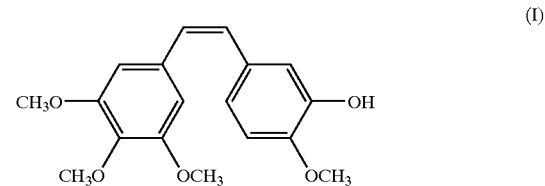

(I)

Compound II has the following formula:

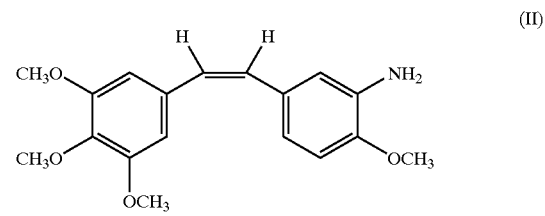

(II)

These combretastatins are barely soluble in water and can be used in the form of a salt exemplified by hydrochloride, acetate, phosphate, methanesulfonate, and the aminoacid salt.

The manufacture of stilbene derivatives which may be in the form of pharmaceutically acceptable salts, hydrates and solvates, and the manufacture of oral and/or parenteral pharmaceutical composition containing the above compound, its inert pharmaceutically acceptable carrier(s) and/or diluent(s), are disclosed in U.S. Pat. Nos. 5,525,632, 5,731,353 and 5,674,906. These patents, which are incorporated herein by reference, disclose that stilbene derivatives, including combretastatin when used alone, have carcinostatic effects in vivo.

It has recently been discovered that the combination of combretastatin and an anticancer agent selected from the group consisting of taxoids, alkylating agents, antimetabolites, vinca alkaloids, platinum compounds, epidophylloptoxins and antibiotics significantly reduces the development of tumor volume over what would be predicted from administration to tumor-infected mammals of each compound alone.

Thus, the present invention is promising as providing a novel antitumor agent, for example, a chemotherapeutic drug against cancer (cancer chemotherapy agent), comprising two types of active ingredients, namely a stilbene derivative and another anticancer compound that can be administered simultaneously or separately.

DETAILED DESCRIPTION OF THE INVENTION

The present invention is directed to an antitumor agent comprising a stilbene derivative and an anticancer agent.

The present invention also encompasses a combination therapy wherein the stilbene derivative and another anticancer agent are prepared as two separate pharmaceutical preparations and administered to a patient in need thereof, simultaneously, semi-simultaneously, separately or spaced out over time.

The tumors against which the antitumor agents of the present invention are administered encompass all sorts of tumors occurring in an animal, especially in a human being. The antitumor agents of the present invention may be used for inhibiting proliferation of tumor cells. The antitumor agents of the present invention are pharmaceutical preparations wherein at least two compounds are used to cure, treat, or suppress tumors.

There is no particular limitation to the form of administration of the antitumor agents. Anticancer agents are routinely administered intravenously, parenterally, and orally. The present invention also encompasses an antitumor agent consisting in the combination of two compounds having distinct forms of administration.

The stilbene derivative used in the present invention has cis-stilbene as a fundamental skeleton and exhibits in vivo tubulin polymerization inhibiting activity and/or an antitumor activity. The stilbene derivatives of the present invention also include prodrugs which may be converted in vivo into a stilbene derivative. All forms of suitable pharmaceutically allowable derivatives, such as salts, esters, amides, solvates (solvation products) and hydrates thereof, may be used as the stilbene derivatives in the present invention, provided that the derivatives exhibit antitumor activity when used in vivo.

Representative stilbene derivatives are shown by one of the following general formulas (I) or (II).

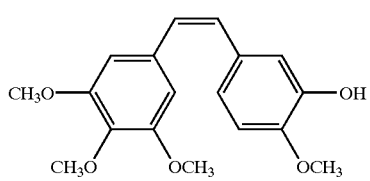

(I)

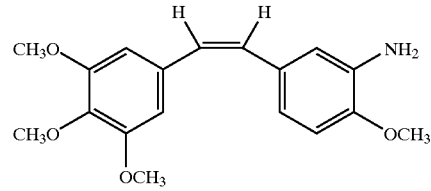

(II)

The amino acids may be enumerated by α-amino acids, β-amino acids and γ-amino acids. Examples of preferred amino acids include glycine, alanine, leucine, serine, lysine, glutamic acid, aspartamic acid, threonine, valine, isoleucine, omithine, glutamine, asparagine, tyrosine, phenylalanine, cysteine, methionine, arginine, -alanine, tryptophan, proline, histidine, etc. In particular, threonine and serine are preferred in view of pharmaceutical effects and safety. Although any one of these amino acids may be of the L-, D- or DL-form, the L-form is preferred.

As described above, the stilbene derivative of the present invention is a compound having a cis-stilbene skeleton in its structure and exhibits tubulin polymerization inhibiting activity and/or an antitumor activity. Such stilbene derivatives are exemplified by combretastatin-A4 disclosed in prior art publications, such as the U.S. Pat. Nos. 4,996,237, 5,561,122 and 5,430,062. The prior art stilbene derivatives, described in these patent publications and combretastatin of formula (II) described in U.S. Pat. Nos. 5,525,632 and 5,731,353, can be used for the stilbene derivatives of the present invention, insofar as they meet the definition for the stilbene derivatives in the present invention.

The above mentioned stilbene derivatives may be manufactured by the routine technique including the method disclosed in the above mentioned known publications.

Among the stilbene derivatives of the present invention, there are salts, esters, and other derivatives of stilbene, and derivatives which may be converted in vivo into the stilbene derivatives, insofar as the stilbene derivatives manifest the above-mentioned objective activities in an animal body.

Among the compounds represented by the general formula (II) above, is the compound represented by the following formula, (IIa):

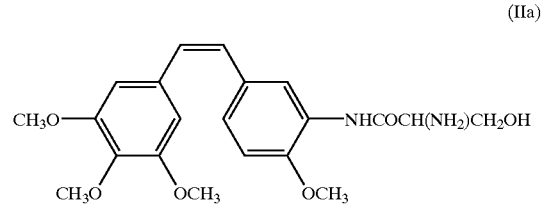

(IIa)

The compound of formula (IIa) is soluble in water and may be in the form of a salt exemplified by hydrochloride, acetate, methanesulfonate and the like.

When the antitumor agent of the present invention is to be used, a stilbene derivative in an amount sufficient to inhibit tumor proliferation may be combined with a compound chosen from the group consisting of taxanes, alkylating agents, antimetabolites, vinca alkaloids, epidophylloptoxins, and antibiotics and administered to the subject, an animal, especially a human being, in need of curing, alleviation of tumors, especially a human being suffering from proliferation of tumor cells, to inhibit the proliferation of said tumor cells.

The present invention also relates to pharmaceutical compositions containing the combinations according to the invention.

The products of which the combination are composed may be administered simultaneously, separately or spaced out over a period of time so as to obtain the maximum efficacy of the combination; it being possible for each administration to vary in its duration from a rapid administration to a continuous perfusion.

As a result, for the purposes of the present invention, the combinations are not exclusively limited to those which are obtained by physical association of the constituents, but also encompass those which permit a separate administration, which can be simultaneous or spaced out over a period of time.

One of the preferred embodiments in the present invention is to use compound IIa in an amount effective to inhibit proliferation of tumor cells in combination with taxotere, doxorubicin, or vincristine to inhibit proliferation of tumor cells.

The inhibition of proliferation of tumor cells means inhibition of proliferation of the tumor cells sensitive to therapy including administration of an effective amount of the stilbene derivatives, such as combretastatin IIa, and taxoid compounds, such as taxol, taxotere and their derivatives to, e.g., a human being suffering from proliferation of tumor cells. In an acceptable case, this administration suppresses proliferation of tumor cells or diminishes the measurable size of the tumors. In an optimum case, the tumor undergoes regression completely.

As described above, there is no particular limitation to the method of administering the antitumor agent of the present invention to the human being, such that it may be administered orally or parenterally, by intravenous, subcutaneous or intramuscular route. For prompt efficacy, parenteral administration, by intravenous and subcutaneous administration, i.e., by infusion, etc. is preferred. In the method for administering the pharmaceutical preparation according to the present invention, the stilbene derivative may be administered simultaneously with the taxoid compound or the two may be sequentially administered in an optional order. The practically desirable method and sequence for administration varies depending on the individual preparation of the stilbene derivative used and the individual preparation of the other anticancer compound used, e.g., taxotere, doxorubicin or a vinca alkaloid, the individual tumor cells being cured, and the individual hosts being treated. The optimum method and sequence for administration of the stilbene derivative and the auxiliary anticancer compound under preset given conditions may be suitably selected by those skilled in the art with the aid of the routine technique and the information contained in the present specification.

The antitumor agent of the present invention is sufficient to be a pharmaceutical preparation comprising the two active ingredients of the present invention contained separately in distinct pharmaceutical preparations used in combination. It is noted that such a pharmaceutical preparation containing other agents (third and fourth medical ingredients and so on) such as other antitumor agents, may naturally be encompassed by the present invention, insofar as the effective ingredients used in the present invention are contained in the pharmaceutical preparation.

As the suitable pharmaceutically acceptable carriers and diluents, used in the antitumor agent of the present invention, those carriers etc., known to those skilled in the art of preparation of pharmaceutical preparations, may be used as appropriate. The antitumor agents of the present invention may be administered parenterally, as discussed above. In this case, the antitumor agent is prepared into an intravenous infusion bag, along with pharmaceutically acceptable carriers by variable methods known to those skilled in the art. Preferably, the pharmaceutical agent is manufactured by a routine technique in e.g., a unit dosage form and in the form of a freeze-dried preparation, and is reprepared in water or other suitable liquid infusion in administration.

The ratio of the two ingredients for the pharmaceutical preparation for the antitumor agent of the present invention may be varied in a wide range, depending on a number of factors, such as a desired amount for administration and on the pharmaceutically acceptable carrier in use. In the pharmaceutical preparation of the antitumor agent of the present invention, approximately 0.01 to 1000 and, in particular, approximately 0.1 to 100 parts by weight of the stilbene derivative, is used with 1 part by weight of the auxiliary anticancer compound. So, when the pharmaceutical preparation in the present invention contains two active ingredients to be administered to the patient, it is administered in an amount which will give the above-defined administration range.

If the pharmaceutical preparation is to be administered stepwise, the above-defined administration range can be set as the average ratio for the separate pharmaceutical preparations.

Preferred Embodiments

The present invention is now explained in more detail with reference to preferred embodiments thereof. It is to be noted that these are given only as an example and are not intended to limit the invention.

The efficacy of a combination may be demonstrated by determination of its therapeutic synergy. A combination manifests therapeutic synergy if it is therapeutically superior to one or other of the constituents used at its optimum dose (T. H. Corbett et al., Cancer Treatment Reports, 66, 1187 (1982)).

The efficacy of a combination may also been demonstrated by comparison of the maximum tolerated dose of the combination with the maximum tolerated dose of each of the separate constituents in the study in question. This efficacy may be quantified, for example by the $\log_{10}$ cell kill, which is determined by the following formula:

$$\log_{10} \text{ cells killed} = T\text{-}C(\text{days})/3.32 \times T_d$$

in which T-C represents the time taken for the cells to grow, which is the mean time in days for the tumors of the treated group (T) to reach a predetermined value (1 g for example) and the tumors of the control group (C) to reach the same value, and $T_d$ represents the time in days needed for the volume of the tumors in the control group to double. (T. H. Corbett et al., Cancer, 40, 2660.2680 (1977); F. M. Schabel et al., Cancer Drug Development, Part B, Methods in Cancer Research, 17, 3–51, New York, Academic Press Inc. (1979)). A product is considered to be active if the $\log_{10}$ cell kill is greater than or equal to 0.7. A product is considered to be very active if the $\log_{10}$ cell kill is greater than 2.8.

The combination, used at its own maximum tolerated dose, in which each of the constituents will be present at a dose generally not exceeding its maximum tolerated dose, will manifest therapeutic synergy when the $\log_{10}$ cells killed is greater than the value of the $\log_{10}$ cells killed of the best constituent when it is administered alone.

In the present invention, a stilbene derivative, such as combretastatin, in an amount sufficient to inhibit tumor proliferation may be used with another anticancer agent such as taxoids, alkylating agents, antimetabolites, vinca alkaloids, epidophylloptoxins, and antibiotics and administered to a mammal, in need of curing, alleviation, or prevention of tumors, especially a human being suffering from proliferation of tumor cells, in order to inhibit the growth of the tumor cells.

The inhibition of proliferation of tumor cells means inhibition of those tumor cells sensitive to therapy including administration of an effective amount of combretastatin and an effective amount of a second anticancer compound as described below to a human being suffering from proliferation of tumor cells. In an acceptable case, this administration suppresses proliferation of tumor cells or diminishes the measurable size of the tumors. In an optimum case, the tumor undergoes regression completely.

As described above, there is no particular limitation to the method of administering the antitumor agents of the present invention to the mammal being treated. They may be administered orally or parenterally, such as by intravenous, subcutaneous or intramuscular route. For prompt efficacy, parenteral administration of combretastatin, such as by intravenous and subcutaneous administration, by infusion, etc. is preferred. In the method for administering the pharmaceutical preparation according to the present invention, combretastatin may be administered simultaneously with another anticancer agent or the two may be sequentially administered in an optional order. In practice, the method and sequence for administration are varied depending on the individual preparation of combretastatin, the individual preparation of the second anticancer agent, the individual tumor cells being cured, and the individual hosts being treated. The optimum method and sequence for administration of combretastatin and the second anticancer agent may be suitably selected by those skilled in the art with the aid of routine technique and the information contained in the present specification.

An efficacious tumor proliferation inhibiting amount of the combretastatin and an anticancer agent selected from the group consisting of taxoids, alkylating agents, antimetabolites, vinca alkaloids, epidophylloptoxins, and antibiotics means a curative unit inhibiting proliferation of the tumor cells sensitive to administration in the human being suffering from proliferation of tumor cells. The practically desirable curative unit is varied depending on the individual dosage forms of combretastatin used, the individual dosage forms of the auxiliary anticancer agent used, the individual tumor cells being cured and the individual hosts being treated. The optimum curative units for preset given conditions may be suitably selected by those skilled in the art with the aid of the curative test units and the information contained in the present specification.

The antitumor agent of the present invention is a pharmaceutical preparation comprising at least combretastatin and one of the anticancer compounds as described above, such that the two active ingredients may be contained as a mixture in a pharmaceutical preparation. However, the two active ingredients in the present invention may also be contained separately in distinct pharmaceutical preparations to be used sequentially and in combination. It is noted that such a pharmaceutical preparation containing other agents (third and fourth medical ingredients and so on) such as other antitumor agents, may naturally be encompassed by the present invention, insofar as the effective ingredients used in the present invention are contained in the pharmaceutical preparation. Moreover, it is possible for carriers, diluents and other substances, pharmaceutically acceptable for any of the pharmaceutical preparations in the present invention (a sole pharmaceutical preparation containing both ingredients in the present invention and separate pharmaceutical preparations separately each containing one of the two ingredients for use in combination) to be contained in the antitumor agent of the present invention.

The present invention is now explained in more detail with reference to preferred embodiments thereof. It is to be noted that these are given only as an examples and are not intended to limit the invention.

Pharmaceutical preparations for infusion were prepared in accordance with the following composition using the combretastatin compounds of formulas (I) and (IIa) shown by the following chemical formulas respectively:

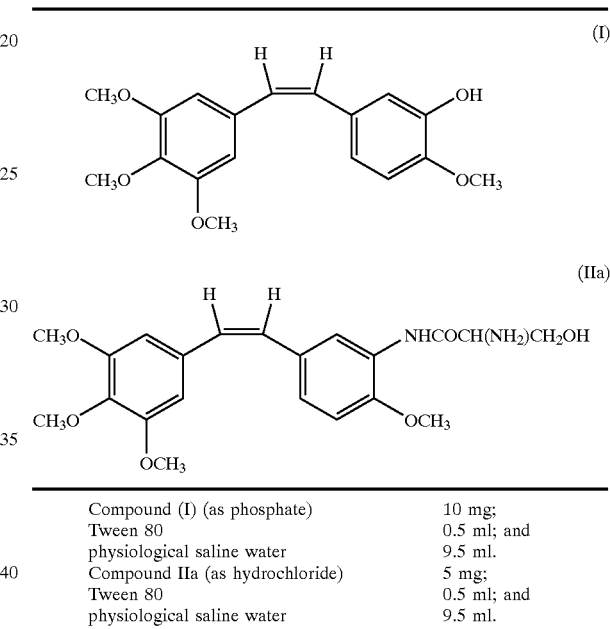

| | |
|---|---|
| Compound (I) (as phosphate) | 10 mg; |
| Tween 80 | 0.5 ml; and |
| physiological saline water | 9.5 ml. |
| Compound IIa (as hydrochloride) | 5 mg; |
| Tween 80 | 0.5 ml; and |
| physiological saline water | 9.5 ml. |

The preparation of taxol, taxotere and their derivatives form the subject, for example, of European Patents EP 0,253,738 and EP 0,253,739 and International Application PCT WO 92/09,589 and are incorporated herein.

Generally, the doses of the taxane used, which depend on factors distinctive to the subject to be treated, are between 1 and 10 mg/kg administered intraperitoneally or between 1 and 3 mg/kg administered intravenously.

Antitumor Effect and Tests on Safety

The efficacy of the combinations on solid tumors were determined experimentally in the following manner:

The animals subjected to the experiment, generally mice, were subcutaneously grafted bilaterally with 30 to 60 mg of a tumor fragment on day 0. The animals bearing tumors were mixed before being subjected to the various treatments and controls. In the case of treatment of advanced tumors, tumors were allowed to develop to the desired size, and animals having insufficiently developed tumors were eliminated. The selected animals were distributed at random to undergo the treatments and controls. Animals not bearing tumors were also subjected to the same treatments as the tumor-bearing animals in order to be able to dissociate the toxic effect from the specific effect on the tumor. Chemotherapy generally began from 3 to 22 days after grafting, depending on the type of tumor, and the animals were observed every day. The different animal groups were weighed 3 or 4 times a week until the maximum weight loss was attained, and the groups were then weighed at least once a week until the end of the trial.

The tumors were measured 2 or 3 times a week until the tumor reached approximately 2 g, or until the animal died if this occurred before the tumor reached 2 g. The animals were autopsied when sacrificed.

The antitumor activity was determined in accordance with different parameters which were recorded such as dose (mg/kg), mode of administration, time of administration, cytotoxicity, toxicity and log cell kill.

For a study of the combinations on leukemias, the animals were grafted with a particular number of cells, and the antitumor activity was determined by the increase in the survival time of the treated mice relative to the controls. The product was considered to be active if the increase in survival time was greater than 27%, and was considered to be very active if the increase was greater than 75% in the case of P388 leukemia.

The results obtained with combinations of combretastatin and various chemotherapeutic agents, such as taxotere (taxane), doxorubicin (antibiotic) vinorelbine (vinca alkaloid), and cisplatinum (platinum compounds), the combinations being used at their optimum dose, are reported.

EXAMPLE 1

In this and the following examples, RPR 258062A corresponds to the hydrochloride salt of compound IIa. The agents were administered intravenously unless otherwise specified.

IN VIVO EVALUATION OF RPR 258062A AND CISPLATINUM

| Agent | Tumor | Schedule days | HNTD Dose mg/kg | T-C days | LcK | RR PR | CR | TFS |
|---|---|---|---|---|---|---|---|---|
| Single agents: | | | | | | | | |
| RPR 258062A | C51 | 12, 16 | 116 | 10 | 1.2 | 6/6 | 0/6 | 0/6 |
| CDDP | | 12, 16 | 6.2 | 16.5 | 1.9 | 5/6 | 0/6 | 0/6 |
| Combination: simultaneous | | | | | | | | |
| RPR 258062A 1st | | 12, 16 | 116 | NA | NA | 6/6 | 6/6 | 6/6 |
| CDDP sequential | | 12, 16 | 10 | | | | | |
| RPR 258062A | | 14 | 58 | 51 | 5.9 | 5/5 | 5/5 | 0/5 |
| CDDP | | 15, 19 | 10 | | | | | |

Abbreviations used:
HNTD = highest nontoxic dose; T-C = tumor growth delay; LcK = log cell kill; RR = response rate; PR = partial response; CR = complete response, TFS = tumor free survivors.
Conclusion: The combination of RPR 258062A and cisplatinum is synergistic.

EXAMPLE 2

IN VIVO EVALUATION OF RPR 258062A AND VINORELBINE

| Agent | Tumor | Schedule days | HNTD Dose mg/kg | T-C days | LcK | RR PR | CR | TFS |
|---|---|---|---|---|---|---|---|---|
| Single agents: | | | | | | | | |
| RPR 258062A | MA13/C | 15, 25 | 150 | 5 | 0.5 | 0/5 | 0/5 | 0/5 |
| Vinorelbine | | 15, 25 | 19.8 | 45.5 | 4.6 | 5/5 | 5/5 | 0/5 |
| Combination - sequential | | | | | | | | |
| RPR 258062A 1st | | 14 | 75 | 84.7 | 8.5* | 5/5 | 5/5 | 2/5 |
| Vinorelbine 2nd | | 15, 25 | 32 | | | | | |

*log cell kill evaluated on the limited number of mice that developed tumor, the other mice in the group were tumor free survivors.
Abbreviations used:
HNTD = highest nontoxic dose; T-C = tumor growth delay; LcK = log cell kill; RR = response rate; PR = partial response; CR = complete response, TFS = tumor free survivors.
Conclusion: The combination of RPR 258062A and vinorelbine is synergistic.

EXAMPLE 3

IN VIVO EVALUATION OF RPR 258062A AND DOCETAXEL

| Agent | Tumor | Schedule days | HNTD Dose mg/kg | T-C days | LcK | RR PR | CR | TFS |
|---|---|---|---|---|---|---|---|---|
| Single agents: | | | | | | | | |
| Docetaxel | MA13/C | 17, 24 | 68 | 26.7 | 3.2* | 6/6 | 4/6 | 3/6 |
| RPR 258062A | | 17, 24 (2x/d) | 242 | 10.8 | 1.3 | 1/6 | 1/6 | 0/6 |
| Combination - sequential | | | | | | | | |
| RPR 258062A | | 16, 23 (2x/d) | 150 | 74.8 | 6.0* | 6/6 | 6/6 | 4/6 |
| Docetaxel | | 17, 24 | 109.6 | | | | | |

*log cell kill evaluated on the limited number of mice that developed tumor, the other mice in the group were tumor free survivors.
Abbreviations used:
HNTD = highest nontoxic dose; T-C = tumor growth delay; LcK = log cell kill; RR = response rate; PR = partial response; CR = complete response, TFS = tumor free survivors.
Conclusion: The combination of RPR 258062A and docetaxel is synergistic.

EXAMPLE 4

IN VIVO EVALUATION OF RPR 258062A AND DOXORUBICIN

| Agent | Tumor | Schedule days | HNTD Dose mg/kg | T-C days | LcK | RR PR | CR | TFS |
|---|---|---|---|---|---|---|---|---|
| Single agents: | | | | | | | | |
| Doxo-rubicin | MA13/C | 15, 22 | 17.4 | 53.5 | 4.5 | 4/6 | 4/6 | 0/6 |
| RPR 258062A | | 15, 22 | 186.0 | 30.2 | 1.3 | 0/6 | 0/6 | 0/6 |
| Combination - sequential | | | | | | | | |
| RPR 258062A | | 15, 21 | 139.6 | 80.6 | 11* | 7/7 | 7/7 | 2/7 |
| Doxo-rubicin | | 16, 22 | 17.4 | | | | | |

*log cell kill evaluated on the limited number of mice that developed tumor, the other mice in the group were tumor free survivors.
Abbreviations used:
HNTD = highest nontoxic dose; T-C = tumor growth delay; LcK = log cell kill; RR = response rate; PR = partial response; CR = complete response, TFS = tumor free survivors.
Conclusion: The combination of RPR 258062A and doxorubicin is synergistic.

EXAMPLE 5

IN VIVO EVALUATION OF RPR 258062A AND CPT-11

| Agent | Tumor | Schedule days | HNTD Dose mg/kg | T-C days | LcK | RR PR | CR | TFS |
|---|---|---|---|---|---|---|---|---|
| Single agents: | | | | | | | | |
| RPR 258062A | C51 | 13–17 (2x/d) | 116.5 | 10.3 | 1.3 | 5/5 | 0/5 | 0/5 |
| CPT-11 (oral) | | 14–17 | 400.0 | 8.7 | 1.1 | 0/5 | 0/5 | 0/5 |
| Combination - sequential | | | | | | | | |
| CPT-11 (oral) | | 13–16 | 400 | 15.1 | 1.9 | 5/5 | 3/5 | 0/5 |
| RPR 258062A | | 17 | 36 | | | | | |

Abbreviations used:
HNTD = highest nontoxic dose; T-C = tumor growth delay; LcK = log cell kill; RR = response rate; PR = partial response; CR = complete response, TFS = tumor free survivors.
Conclusion: The combination of RPR 258062A and CPT-11 induces a greater number of complete responses and a higher log cell kill.

What is claimed is:

1. A pharmaceutical combination comprising an effective amount of an anticancer compound selected from the group consisting of docetaxel, doxorubicin, and vinorelbine in combination with an effective amount of combretastatin for the treatment of solid tumors, wherein said combretastatin has the following formula:

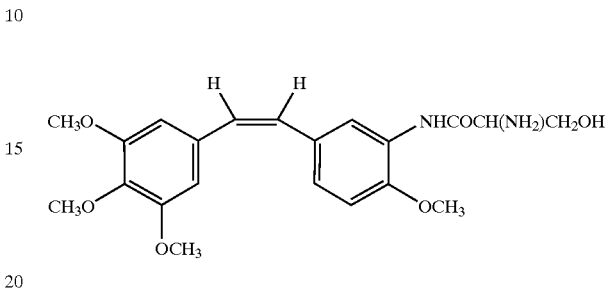

2. The combination according to claim 1, wherein said combretastatin is in the form of a hydrochloride salt.

3. The combination according to claim 1 or claim 2, wherein said anticancer compound is docetaxel.

4. The combination according to claim 1 or claim 2, wherein said anticancer compound is doxorubicin.

5. The combination according to claim 1 or claim 2, wherein said anticancer compound is vinorelbine.

6. A method of treating solid tumors comprising administering sequentially first an effective amount of combretastatin as claimed in claim 1 or in claim 2 and then an effective amount of docetaxel to a subject in need thereof, wherein the combination exhibits therapeutic synergy in the treatment of solid tumors.

7. A method of treating solid tumors comprising administering sequentially first an effective amount of combretastatin as claimed in claim 1 or in claim 2 and then an effective amount of vinorelbine to a subject in need thereof, wherein the combination exhibits therapeutic synergy in the treatment of solid tumors.

8. A method of treating solid tumors comprising administering sequentially first an effective amount of combretastatin as claimed in claim 1 or in claim 2 and then an effective amount of doxorubicin to a subject in need thereof, wherein the combination exhibits therapeutic synergy in the treatment of solid tumors.

* * * * *